United States Patent
Dudding et al.

(10) Patent No.: US 6,456,887 B1
(45) Date of Patent: Sep. 24, 2002

(54) LOW ENERGY CONSUMPTION RF TELEMETRY CONTROL FOR AN IMPLANTABLE MEDICAL DEVICE

(75) Inventors: Charles H. Dudding, Lino Lakes; Gregory J. Haubrich, Champlin, both of MN (US)

(73) Assignee: Medtronic, Inc., Minneapolis, MN (US)

(*) Notice: Subject to any disclaimer, the term of this patent is extended or adjusted under 35 U.S.C. 154(b) by 124 days.

(21) Appl. No.: 09/736,625

(22) Filed: Dec. 14, 2000

(51) Int. Cl.[7] ............................................. G08C 17/02
(52) U.S. Cl. .............................. 607/60; 607/31; 607/32
(58) Field of Search .............................. 607/30, 32, 60, 607/31; 128/903; 340/573.1; 331/1 R; 455/343, 182.2

(56) References Cited

U.S. PATENT DOCUMENTS 4,745,371 A * 5/1988 Haine ......................... 331/1 A

* cited by examiner

Primary Examiner—Kennedy Schaetzle
(74) Attorney, Agent, or Firm—Girma Wolde-Michael

(57) ABSTRACT

In an implantable medical device, a frequency synthesizer employed in the RF transceiver of the IMD operating system functions in a PLL LOCK mode wherein the VCO frequency is governed by the PLL and an energy saving HOLD mode wherein the PLL is not operational and the VCO generated carrier frequency can drift over time. The PLL circuit is powered up and coupled with a control voltage input and the output of the VCO to develop a frequency control voltage stored by a capacitive loop filter during initial LOCK portions of both uplink and downlink telemetry transmission time periods. A frequency modulation (FM) input of the VCO receives data bit modulation voltages that modulates the carrier frequency during uplink transmission of patient data. During the HOLD portion of a downlink telemetry transmission, an AFC algorithm is enabled and derives a frequency correction value from the difference in frequency of the constant received carrier frequency and the drifting VCO generated carrier frequency, and the frequency correction value is applied to the VCO FM input to compensate for loop filter capacitor discharge of the control voltage causing the drift. The AFC algorithm derived frequency correction value is stored in memory and is also applied during the HOLD portion of an uplink telemetry transmission to the VCO FM input to compensate for loop filter capacitor discharge of the control voltage causing the drift. In addition, a recharge current is applied to the capacitive loop filter.

25 Claims, 4 Drawing Sheets

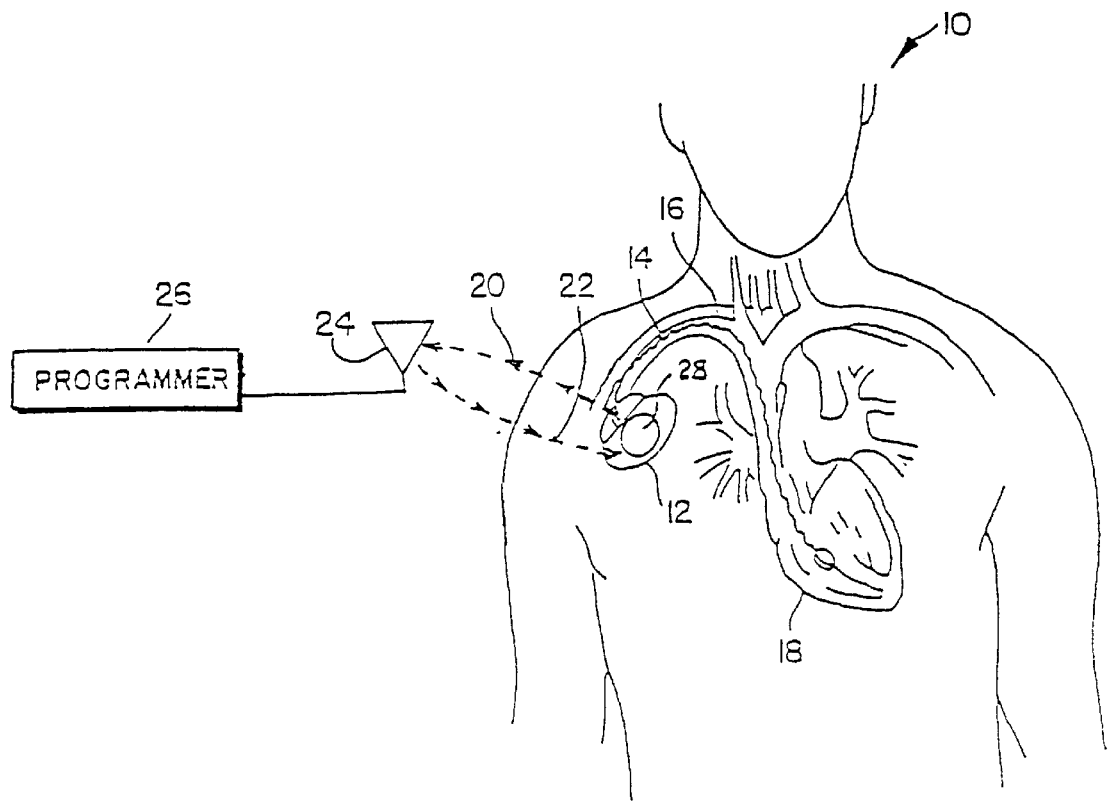
FIG. 1
FIG. 2
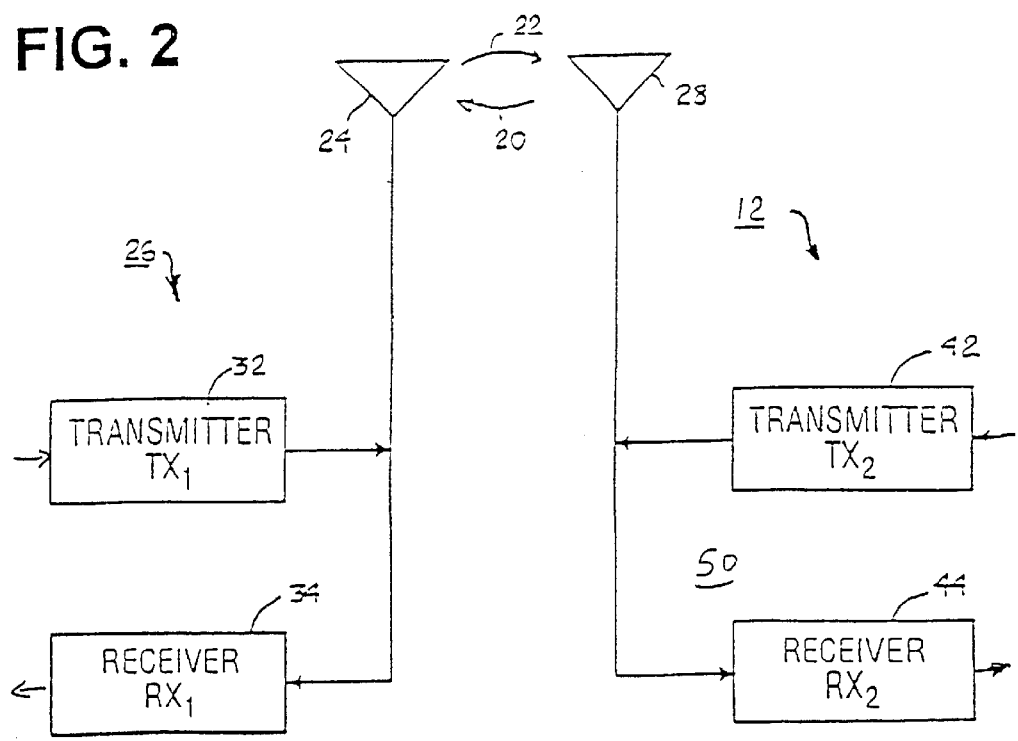

LOW ENERGY CONSUMPTION RF TELEMETRY CONTROL FOR AN IMPLANTABLE MEDICAL DEVICE

FIELD OF THE INVENTION

The present invention relates generally to the field of implantable medical devices, and more particularly to low energy uplink and downlink telemetry control for an implantable medical device (IMD) telemetry transceiver.

BACKGROUND OF THE INVENTION

At present, a wide variety of IMDs are commercially released or proposed for clinical implantation that are programmable in a variety of operating modes and are interrogatable using RF telemetry transmissions. Such medical devices include implantable cardiac pacemakers, cardioverter/defibrillators, cardiomyostimulators, pacemaker/cardioverter/defibrillators, drug delivery systems, cardiac and other physiologic monitors, electrical stimulators including nerve and muscle stimulators, deep brain stimulators, and cochlear implants, and heart assist devices or pumps, etc.

Typically, certain therapy delivery and monitoring operational modes and parameters of the IMD are altered temporarily or chronically in a non-invasive (i.e. non-surgical) manner using downlink telemetry transmission from an external programmer of programming and interrogation commands (herein referred to as "downlink telemetry data"). Moreover, a wide variety of real time and stored physiologic and non-physiologic data (referred to collectively herein as "patient data") is uplink telemetered by the IMD to the programmer in response to a downlink telemetered interrogation command.

The telemetry transmission system that has evolved into common use currently relies upon the generation of low amplitude magnetic fields by current oscillating in an LC circuit of an RF telemetry antenna in a transmitting mode and the sensing of currents induced a closely spaced RF telemetry antenna in a receiving mode. Short duration bursts of the carrier frequency using a variety of telemetry transmission and encoding formats are transmitted through the patient's skin between the antennae and transceiver circuits in a programming head overlying the skin and the IMD under the skin. In the current MEDTRONIC® product line, the RF carrier frequency is set at 175 kHz and the RF telemetry antenna of the IMD is typically coiled wire wound about a ferrite core that is located within the hermetically sealed enclosure. The hermetically sealed enclosure also typically contains a battery power source and circuitry for controlling the operation of the IMD and a reed switch or MAGFET that is responsive to an externally applied magnetic field within the external programming head to enable decoding of downlink telemetry transmissions by and transmission of uplink telemetry from the IMD.

In an uplink telemetry transmission from an IMD, it is desirable to limit the current drain from the IMD battery as much as possible simply to prolong IMD longevity. As the technology advances, IMDs become ever more complex in possible programmable operating modes, menus of available operating parameters, and capabilities of monitoring increasing varieties of physiologic conditions and electrical signals. These complexities place ever increasing demands on the programming and interrogation system and the medical care providers using them. Thus, as device operating and monitoring capabilities multiply, it is desirable to be able to transmit out ever increasing volumes of data in real time or in as short a transmission time as possible with high reliability and immunity to spurious noise. Moreover, it is desirable to eliminate the need for the magnetic field coupling between the programming head and the IMD and to allow secure programming and interrogation to take place at greater distances between the IMD and programmer antennae.

As a result of these considerations, many RF telemetry transmission data encoding schemes have been proposed or currently are used that increase security and the data transmission rate as well as the safe operating distance between the IMD and programmer antennae. One way to increase data transmission capacity is to increase the RF carrier frequency and the bandwidth allocated to an active transmission channel into the MHz range as set forth in commonly assigned U.S. Pat. No. 5,861,019 and in pending U.S. patent application Ser. No. 09/302,932 for a "Telemetry System for Implantable Medical Devices", filed Apr. 30, 1999, by Villesca et al.

The above-referenced 175 kHz RF carrier frequency is generated employing a relatively simple low current consuming L-C tank circuit and switching circuitry. But, a high frequency RF generator is necessary to generate the high frequency RF carrier signal in the MHz range, and it is necessary to carefully control the generator to prevent frequency drift without unduly increasing current consumption from the IMD battery.

Similar problems exist in other non-IMD communication systems operating with a particular RF carrier frequency or within particular allocated frequency bands in FM transmission and reception modes as set forth in U.S. Pat. Nos. 4,521,918, 4,955,075, 5,335,365, 5,748,103, 5,767,791 and 5,944,659, for example. Typically, a battery powered remote device, e.g., an external patient monitor or a mobile cellular phone, is powered by a battery and communicates with remote, line powered equipment either periodically, in the case of a monitor, or, in the case of a cellular phone, when a user answers an incoming call or initiates an outgoing call. The battery powered monitor or cellular phone employs a frequency synthesizer to generate the RF carrier signal during transmission of data or voice, and the frequency synthesizer typically comprises a voltage controlled oscillator (VCO) and a phase lock loop (PLL) circuit that regulates the frequency of the generated RF signal. The PLL circuit operates in a feedback path employing a reference frequency to develop a PLL control voltage maintained on a capacitive loop filter that is applied to a control input of the VCO which responds by oscillating at the RF carrier frequency established by the control voltage. In the transmission mode, the RF carrier frequency is modulated in frequency by the superimposition of a data or voice voltage on the control voltage, thereby increasing or decreasing the VCO generated carrier frequency.

The PLL circuit consumes battery energy, and so, it is often only operated to stabilize the VCO and is then turned off during data or voice transmission or during a standby mode, as suggested in the above-referenced '365 patent. In addition, it is proposed in the above-referenced '075 patent to employ automatic frequency control (AFC) during reception of the RF carrier frequency of a received signal to stabilize the VCO frequency. In the receive mode, the VCO frequency is initially stabilized by the PLL circuit, and then the AFC is substituted for the PLL, which is disconnected from the VCO and/or powered off.

It is also proposed to remove power from the PLL circuit or disconnect it from the VCO during the transmission mode after the VCO voltage has stabilized to within acceptable frequency tolerances and provides the control voltage on the capacitive loop filter. However, the control voltage stored by the loop filter tends to is decline due to current leakage over time, and so it is necessary to periodically power up and/or reconnect the PLL circuit to the loop filter and VCO to restore the control voltage as described in the above-referenced '918 patent. Or, the control voltage that is developed in a transmit or receive mode is stored and is used during the standby mode to maintain the control voltage via a feedback loop under the control of a microcomputer as described in the above-referenced '365 patent. The feedback loop employs A/D and D/A converters and is not used during the transmit or receive modes because it would inherently introduce noise on the transmitted or received signal. The circuitry of such a feedback loop also consumes space on the RF module that must be fitted into the limited space within the IMD housing.

Accordingly, it is an objective of the present invention to save IMD battery energy during telemetry sessions while still generating the high RF carrier frequency that is required to provide the data transmission rate required between the IMD and the external programmer at a distance from the patient and also meets the standards established by regulatory agencies for accuracy, stability and patient safety.

SUMMARY OF THE INVENTION

In accordance with the present invention, the frequency synthesizer employed in the RF transceiver of the IMD operating system functions in a PLL LOCK mode wherein the VCO frequency is governed by the PLL and an energy saving HOLD mode wherein the PLL is not operational, and control voltage dissipation is compensated for during uplink and downlink telemetry transmissions.

The RF transceiver is normally dormant and powered down until an event occurs that signifies the start of a telemetry session, the telemetry session involving operating the IMD and the external programmer in successive uplink and downlink telemetry transmissions. The PLL circuit is powered up and coupled with a control voltage input and the output of the VCO to develop a frequency control voltage stored by a capacitive loop filter during initial LOCK portions of both uplink (transmitting) and downlink (receiving) telemetry transmission time periods. The VCO also has a frequency modulation (FM) input that receives the data bit modulation voltage that modulates the carrier frequency during uplink transmission of patient data. The PLL circuit is disconnected from the VCO and the loop filter and is placed in a low energy state during the subsequent HOLD portions of both uplink and downlink telemetry transmission time periods when the control voltage and the resulting VCO carrier frequency have stabilized sufficiently.

During the HOLD portion of a downlink telemetry transmission, the VCO generated carrier signal and the received signal are mixed, and the telemetered information of the RF signal that is modulated and transmitted by the programmer is demodulated. An AFC algorithm is enabled during the HOLD portion of the downlink telemetry transmission and derives a frequency correction value from the difference in frequency of the average frequency of the received carrier frequency and the VCO generated carrier frequency. The frequency correction value is applied to the VCO to compensate for VCO frequency tolerances and for loop filter capacitor discharge of the control voltage to thereby drive the VCO generated carrier frequency toward the average carrier frequency of the received carrier signal.

The frequency correction value derived by the AFC algorithm is converted to a frequency correction voltage value that is applied to the FM input of the VCO. The correction voltage value is effectively summed with the decreasing loop filter capacitor voltage by the VCO, and the VCO responds to the summed voltages to generate the VCO carrier frequency so that the VCO generated carrier signal remains relatively constant over the HOLD portion while receiving a downlink telemetry transmission. Each successively determined correction voltage value increases with time in as the control voltage stored in the loop filter capacitor discharges.

Preferably, drift of the VCO generated carrier frequency during the HOLD portion of the uplink telemetry transmission time period is compensated for through use of the frequency correction values developed in a preceding HOLD portion of a downlink telemetry transmission. The frequency correction values periodically developed by the AFC algorithm during the HOLD portion of a downlink telemetry transmission are processed by a transmit drift compensation circuit. The stored frequency correction values of the data set are each successively retrieved and converted to a correction voltage value that is summed with the modulation voltage of the data signal that is applied to the FM input of the VCO. In this case, the sum of the correction voltage value and the modulation voltage of the patient data signal (when present) is effectively summed with the decreasing loop filter capacitor voltage by the VCO. Again, the VCO responds to the summed voltages applied to the two inputs to generate the VCO carrier frequency so that the VCO generated carrier signal remains relatively constant over the HOLD portion of the uplink telemetry transmission.

In a further preferred embodiment, a fixed recharge current is applied by a recharge current source to the loop filter capacitor to compensate for voltage discharge during both the LOCK and HOLD portions of each uplink and downlink telemetry transmission time period. The fixed recharge current value that is derived and stored in IMD memory tends to recharge the loop filter capacitor toward the required control voltage and thereby compensates for current leakage. In one variation of this embodiment, the rate of change of the correction voltage values that are derived by the AFC algorithm during the HOLD portion of the downlink telemetry transmission time period is calculated and stored in IMD memory as a fixed recharge current value. In another variation of this embodiment, the rate of capacitor discharge of the loop filter capacitor over time is measured following assembly of the IMD, and the recharge current value is derived and stored in memory as a function of the rate of capacitor discharge.

Preferably, both the relatively coarse recharge function of the recharge current source and the fine correction functions enabled by the AFC algorithm and applied in real time or retrieved from memory in downlink and uplink telemetry transmission time periods, respectively, are employed together.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 1 is a simplified schematic view of uplink and downlink telemetry transmissions between an exemplary IMD implanted in a patient's body and an external programmer;

FIG. 2 is a simplified block diagram of major functional uplink and downlink telemetry transmission functions of the external programmer and IMD of FIG. 1;

DETAILED DESCRIPTION OF THE PREFERRED EMBODIMENTS OF THE INVENTION

The present invention can be implemented in any IMD having uplink and downlink telemetry capabilities. At present, a wide variety of IMDs are commercially released or proposed for clinical implantation. Such medical devices include implantable cardiac pacemakers as well as ICDs, pacemaker-cardioverter-defibrillators, drug delivery pumps, cardiomyostimulators, cardiac and other physiologic monitors, nerve and muscle stimulators, deep brain stimulators, cochlear implants, artificial hearts, etc. As the technology advances, IMDs become ever more complex in possible programmable operating modes, menus of available operating parameters, and capabilities of monitoring increasing varieties of physiologic conditions and electrical signals which place ever increasing demands on the telemetry transmission system. It is also contemplated that the present invention may be implemented in more than one IMD implanted within the same patient to enable communication between them.

Figure 3:
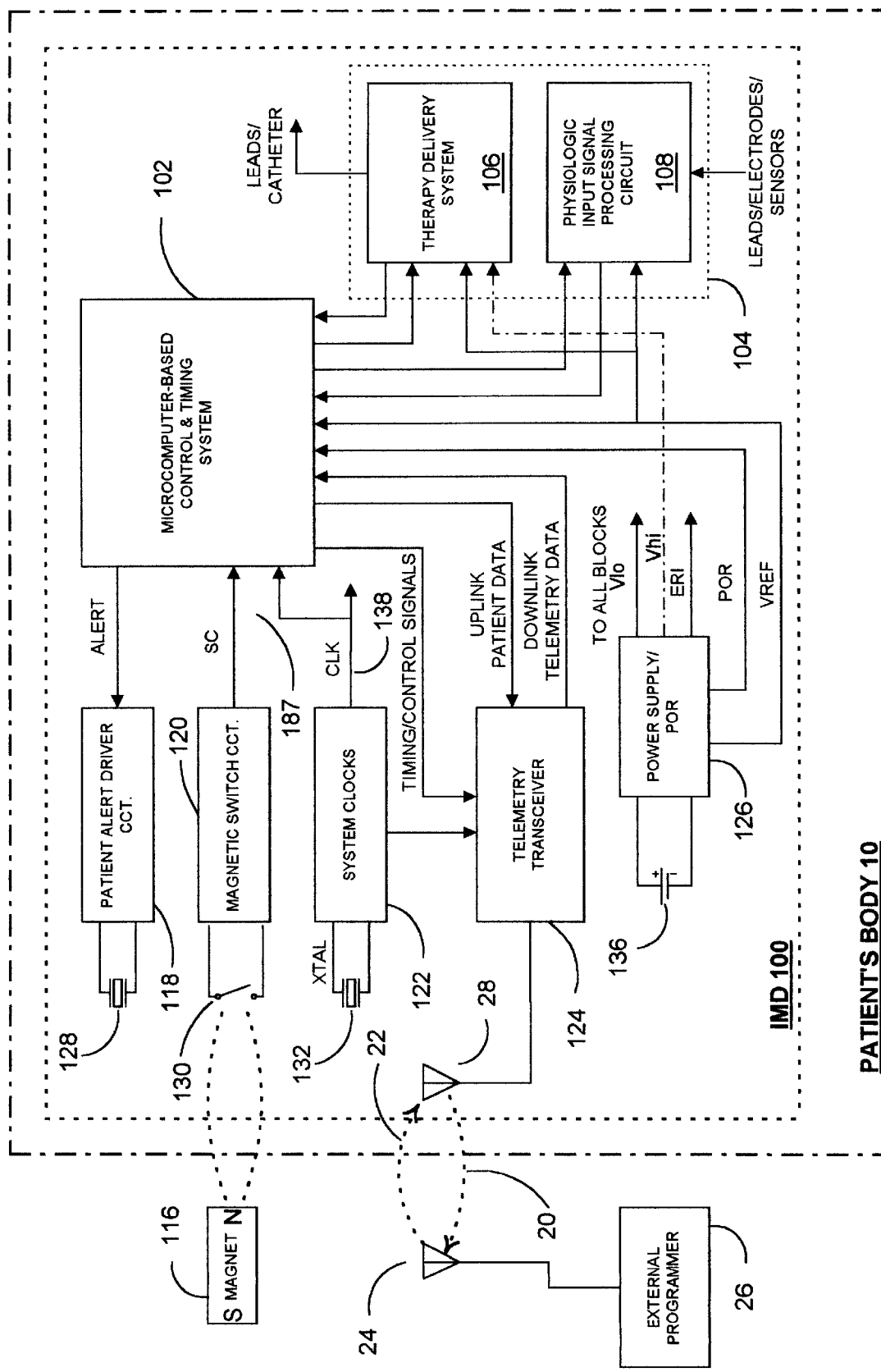
FIG. 3 is a block diagram of a system architecture of an exemplary IMD that incorporates delivery of a therapy and/or physiologic input signal processing in which the telemetry system of the present invention is incorporated.

FIG. 1 illustrates bi-directional telemetry communication between an external programmer 26 and an IMD 100, e.g., an ICD, hemodynamic monitor or cardiac pacemaker IPG 12 and an endocardial lead 14, in accordance with one embodiment of the present invention. The IPG 12 is implanted in the patient 10 beneath the patient's skin or muscle and is typically oriented to the skin surface. The IPG 12 is electrically coupled to the heart 18 of the patient 10 through pace/sense or cardioversion/defibrillation electrodes and lead conductor(s) of at least one endocardial lead 14 coupled to the IPG connector in a manner known in the art. The IPG 12 contains a battery and an operating system powered by the battery that may employ a microcomputer or a digital state machine for timing and controlling device functions in accordance with a programmed operating mode. An exemplary operating system enclosed within IPG 12 is depicted in FIG. 3 and described further below. When the IPG 12 is provides cardiac pacing functions, its operating system memory registers in RAM for storing a variety of programmed-in operating mode and parameter values that are used by the operating system. The memory registers may also be used for storing patient data compiled from sensed cardiac activity and/or relating to device operating history or sensed physiologic parameters for telemetry out on receipt of downlink transmitted retrieval or interrogation command. The operating system also includes sense amplifiers for detecting cardiac signals, pulse generating output circuits for delivering pacing pulses to at least one heart chamber of the heart 18, and optionally includes patient activity sensors or other physiologic sensors for sensing the need for cardiac output and modulating pacing parameters accordingly in a manner well known in the prior art. When the IPG 12 is an ICD, it includes one or more high power cardioversion/defibrillation output capacitor, electronic circuitry coupled to the sense amplifiers for detecting and discriminating pathologic and/or non-pathologic arrhythmias from one another and providing other functions, high voltage electronic charging circuitry for charging the output capacitor(s) from a battery voltage to a higher voltage, and electronic switching circuitry for dumping the charge built up on the output capacitor(s) through the cardioversion/defibrillation electrodes. Such a pacing or ICD IPG 12 is described in detail in commonly assigned U.S. Pat. Nos. 5,626,620 or 5,931,857, respectively.

The IPG operating system also includes telemetry circuitry and a telemetry antenna 28, which can take the form of a surface mounted antenna described in the above-referenced '019 patent or an antenna enclosed within or mounted to the IPG connector. It is desirable to reduce the size of the IPG while increasing its functional capabilities and prolonging battery life to increase longevity. In accordance with the present invention, the current consumption of certain transceiver circuits is decreased. By way of background to place this in context, the IPG telemetry system and functions are first described as follows. For convenience of description, the preferred embodiments are described as follows using RF downlink telemetry (DT) transmissions 22 and uplink telemetry (UT) transmissions 20. The terms "telemeter", "telemetry transmission" and the like are intended to embrace any action and manner of communicating and conveying patient data and downlink telemetry data between the IPG and any external monitoring device or programmer 26 in the UT direction and the DT direction, respectively.

Downlink telemetry data packets and patient data packets are transmitted between the IPG RF telemetry antenna 28 within or on or extending from a surface of the IPG 12 and an external RF telemetry antenna 24 associated with the external programmer 26. Preferably, a high frequency carrier signal in the range of 402 to 405 MHz is employed and it is not necessary that the external RF telemetry antenna 24 be located close to the patient's skin overlying the IPG 12. Instead, the external RF telemetry antenna 24 can be located on the case of the external programmer some distance, e.g., about two to five meters, from the patient 10. For example, the external programmer 26 and external RF telemetry antenna 24 may be on a stand a few meters or so away from the patient 10 as described, for example, in the above referenced '019 patent and in commonly assigned U.S. Pat. Nos. 5,683,432 and 5,843,139. Moreover, the patient 10 may be active and could be exercising on a treadmill or the like during an uplink telemetry interrogation of real time ECG or physiologic parameters. The programmer 26 may also be designed to universally program existing IPGs that employ the conventional ferrite core, wire coil, RF telemetry antenna of the prior art and therefore also have a conventional programmer RF head and associated software for selective use with such IPGs.

In an uplink telemetry transmission 20, the external RF telemetry antenna 24 operates as a telemetry receiver antenna, and the IPG RF telemetry antenna 28 operates as a telemetry transmitter antenna. Conversely, in a downlink telemetry transmission 22, the external RF telemetry antenna 24 operates as a telemetry transmitter antenna, and the IPG RF telemetry antenna 28 operates as a telemetry receiver antenna.

FIG. 2 illustrates certain of the functional telemetry transmission blocks of the external programmer 26 and IPG 12 of FIG. 1. The external RF telemetry antenna 24 within the programmer 26 is coupled to a telemetry transceiver comprising a telemetry transmitter 32 and telemetry receiver 34. The programmer telemetry transmitter 32 and telemetry receiver 34 are coupled to control circuitry and registers operated under the control of a microcomputer and software as described in the above-referenced '139 patent, for example. Similarly, within the IPG 12, the IPG RF telemetry antenna 28 is coupled to a telemetry transceiver comprising a telemetry transmitter 42 and telemetry receiver 44 that are further described below with reference to FIGS. 3 and 4.

In an uplink telemetry transmission 20, the telemetered patient data may be encoded in any of the telemetry formats. In a particular example described below, the data encoding or modulation is in the form of frequency shift key (FSK) modulation of the carrier frequency, for example. To initiate an uplink telemetry transmission 20, the telemetry transmitter 32 in external programmer 26 is enabled in response to a user input to generate an INTERROGATE command in a downlink telemetry transmission 22. The INTERROGATE command is received and demodulated in receiver 44 and applied to an input of the IMD central processing unit (CPU), e.g. a microcomputer (not shown). The IMD microcomputer responds by forwarding the requested patient data to the transmitter 42 that generates the encoded uplink telemetry transmission 20.

The uplink and downlink telemetry transmissions 20 and 22 follow a telemetry protocol that formulates, transmits and demodulates downlink telemetry data packets and patient data packets each comprising a bit stream of FSK modulated data bits. The data packets are formulated of an FSK data bit stream with a preamble, data and error checking data bits. A carrier frequency centered in a 300 kHz band between 402 MHz and 405 MHz is modulated in frequency or frequency shifted up representing a data bit "1" or shifted down to represent the data bit "0". Each uplink and downlink telemetry transmission 20 and 22 takes place during a respective uplink telemetry transmission time period and downlink telemetry transmission time period.

FIG. 3 depicts a system architecture of an exemplary IMD 100 implanted into a patient's body 10 that provides delivery of a therapy and/or physiologic input signal processing. The typical IMD 100 has a system architecture that is constructed about a microcomputer-based control and timing system 102 which varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of IMD 100 can be accomplished with dedicated circuit hardware or state machine logic rather than a programmed microcomputer.

The IMD 100 also typically includes patient interface circuitry 104 for receiving signals from sensors or electrodes located at specific sites of a patient's body 10 and/or delivering a therapy to a site of the patient's body 10. The typical patient interface circuitry 104 therefore comprises a therapy delivery system 106 and a physiologic input signal processing circuit 108 or simply one or the other.

The therapy delivery system 106 can be configured to deliver electrical stimulation to the body, e.g., cardioversion/defibrillation shocks and/or cardiac pacing pulses delivered to the heart, or other electrical stimulation delivered to the brain, other organs, selected nerves, the spinal column, the cochlea, or muscle groups, including skeletal muscle wrapped about the heart. Or the therapy delivery system 106 can be configured as a drug pump delivering drugs into organs for therapeutic treatment or into the spinal column for pain relief. Or therapy delivery system 106 can be configured to operate an implantable heart assist device or pump implanted in patients awaiting a heart transplant operation.

It will be understood that most of these therapy delivery IMDs also have a physiologic input signal processing circuit 108 that processes physiologic signals that are used to trigger or modulate therapy delivery and are stored as physiologic signal data for later retrieval as described above. The physiologic input signal processing circuit 108 is coupled to electrical signal sense electrodes and/or physiologic sensors on or in the housing of the IMD 100 or situated at sites distanced from the IMD housing, typically in distal portions of elongated leads. The sensors or electrodes located outside the housing are coupled by conductors to feedthrough pins of feedthroughs extending through the housing wall. Certain physiologic sensors or sense electrodes can be mounted to a connector assembly so that the conductors are quite short. Typically, however, the conductors include the elongated conductors of leads extending to the remotely situated physiologic sensors and sense electrodes.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Or the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLED IHM coupled with a capacitive pressure and temperature sensing lead and EGM sense electrodes of the type described in commonly assigned U.S. Pat. No. 5,564,434 is an example of the latter.

These are merely exemplary configurations of IMD 100, therapy delivery system 106, and physiologic input signal processing circuit 108 for therapy delivery and/or monitoring. In all cases, the micro-computer-based control and timing system 102 governs all operating functions employing an appropriate, programmable operating algorithm. FIG. 1 also depicts other typical components common to an IMD 100 in any of these therapy delivery and/or monitoring configurations.

All current IMDs rely upon a source of electrical energy to power the IMD operating system including the circuitry of IMD 100 and to power any electromechanical devices, e.g., valves, pumps, etc. of a substance delivery IMD, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 1.

In addition, in certain IMDs, an audible patient alert warning or message is generated by a transducer 128 when driven by a patient alert driver 118 to advise of device operations, battery power level or a monitored patient condition. In ICDs, the patient may be warned of the detection of a malignant tachyarrhythmia and the imminent delivery of a cardioversion/defibrillation shock to enable the patient to assume a resting position prior to delivery.

Virtually all current electronic IMD circuitry employs clocked CMOS digital logic ICs that require a clock signal CLK provided by a piezoelectric crystal 132 and system clock 122 coupled thereto. In FIG. 1, each CLK signal generated by system clock 122 is routed to all applicable clocked logic via a clock tree 138. The system clock 122 provides one or more fixed frequency CLK signal that is independent of the battery voltage over an operating battery voltage range for system timing and control functions and in formatting uplink telemetry signal transmissions in the telemetry I/O circuit 124.

In the IMD 100, uplink and downlink telemetry capabilities are provided to enable communication with either a remotely located external medical device or a more proximal medical device on the patient's body or another IMD in the patient's body as described above with respect to FIGS. 1 and 2.

The RAM registers may be used for storing the patient data comprising physiologic patient data compiled from sensed cardiac activity or sensed physiologic parameters and non-physiologic patient data relating to device operating history for uplink telemetry transmission on receipt of a retrieval or interrogation instruction via a downlink telemetry transmission. The criteria for triggering such patient data storage can also be programmed in via downlink telemetry transmitted instructions and parameter values The physiologic data storage is either triggered on a periodic basis or by detection logic within the physiologic input signal processing circuit 108 upon satisfaction of certain programmed-in event detection criteria. In some cases, the IMD 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted IMD 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later initiated telemetry session.

In addition, real-time generated physiologic patient data can be transmitted by uplink RF telemetry from the IMD 100 to the external programmer or other remote medical device 26 in response to a downlink telemetered interrogation command. The real-time physiologic data typically includes real time sampled signal levels, e.g., intracardiac electrocardiogram amplitude values, and sensor output signals.

The non-physiologic patient data that can be transmitted by uplink RF telemetry from the IMD 100 to the external programmer or other remote medical device 26 includes currently programmed device operating modes and parameter values, battery condition, device ID, patient ID, implantation dates, device programming history, real time event markers, and the like. In the context of implantable pacemakers and ICDs, such non-physiologic patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies.

Figure 4:
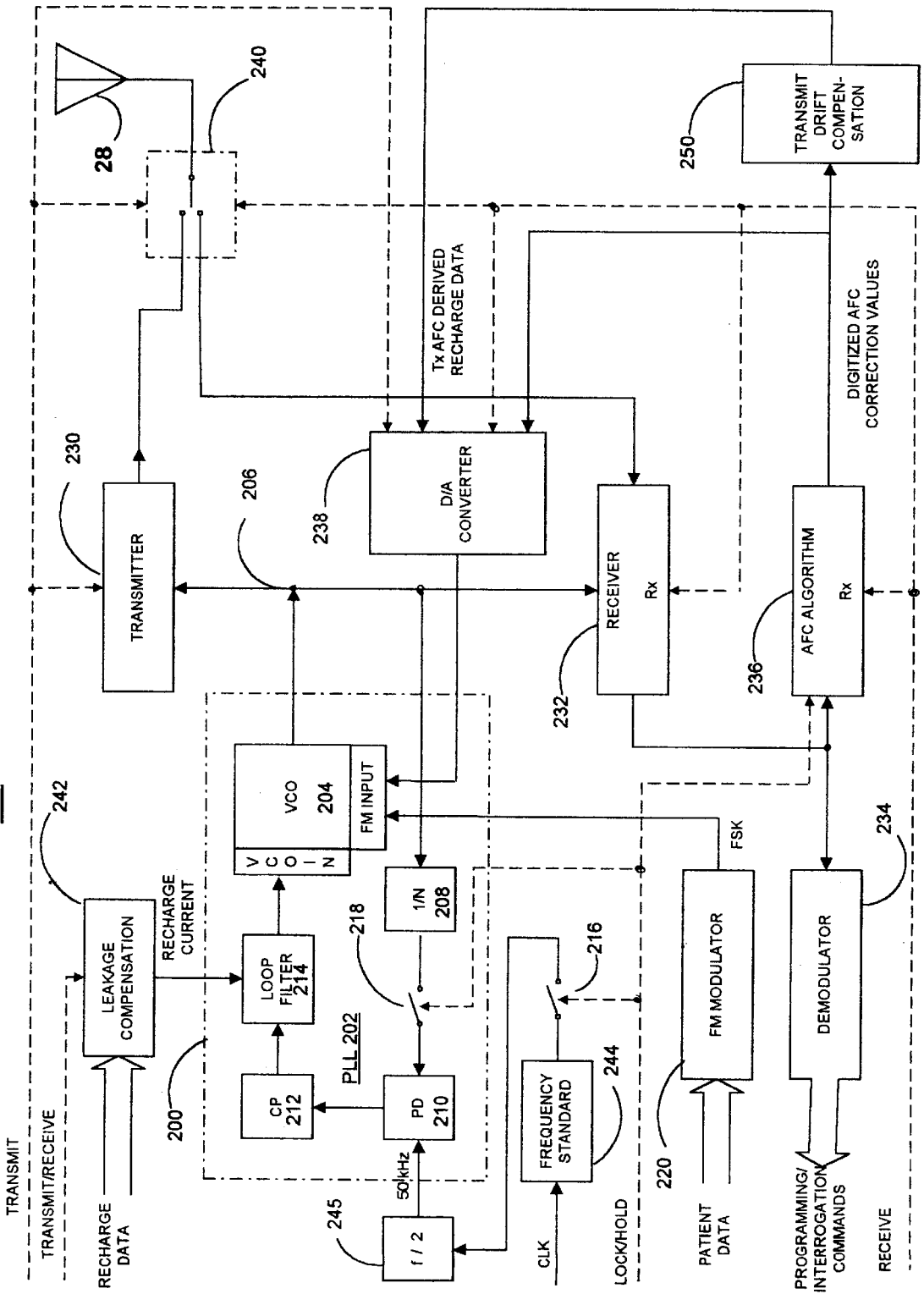
FIG. 4 is a simplified block diagram of the RF telemetry transceiver of the present invention that is incorporated into the exemplary IMD of FIG. 3.
Figure 5:
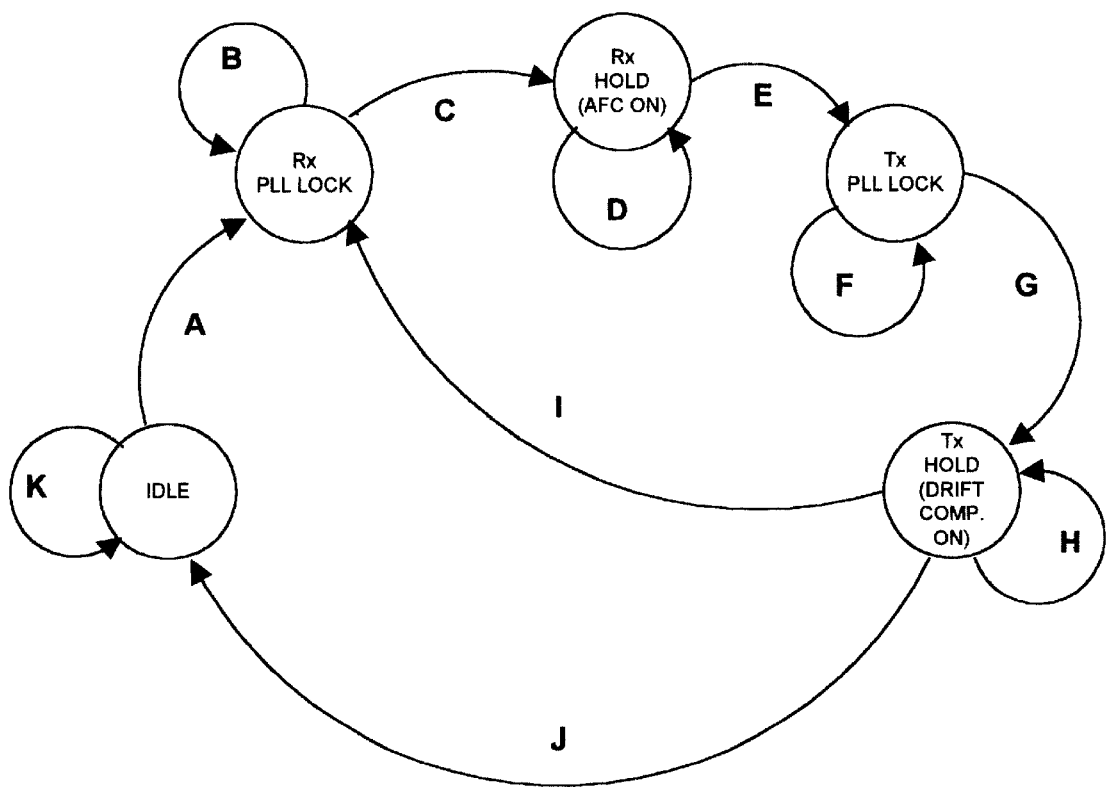
FIG. 5 is a state diagram illustrating the operation of the RF telemetry transceiver of the present invention illustrated in FIG. 4.

In accordance with the present invention, the battery energy expended in uplink telemetry transmissions of such IMD developed patient data and downlink telemetry transmissions of programming and interrogation commands is conserved employing the telemetry transceiver 124 illustrated in FIG. 4 operating in accordance with the state diagram of FIG. 5. Each uplink and downlink telemetry transmission time period is divided into an initial LOCK portion and a subsequent HOLD portion. Programming/interrogation commands are received after the commencement of and during the subsequent HOLD portion of each downlink telemetry transmission. Similarly, encoded PATIENT DATA packets are transmitted by transmitter 230 after the commencement of and during the subsequent HOLD portion of each uplink telemetry transmission.

Telemetry transceiver 124 preferably operates in accordance with a protocol that causes timing and control signals to be provided such that patient data is transmitted during an uplink telemetry transmission and downlink telemetry data is received during a downlink telemetry transmission. The timing and control signals pertinent to the present invention include the TRANSMIT enabling signal, the LOCK/HOLD state signal, and the RECEIVE enabling signal generated at appropriate times by a control and timing system which can be either resident within transceiver 124 or received from timing and control system 102.

The TRANSMIT control signal enables the transmitter 230 to transmit FSK modulated PATIENT DATA packets and couples the output of the transmitter 230 to the antenna 28 through switch 240. In one preferred embodiment, the TRANSMIT control signal also enables the D/A converter 238 to receive stored AFC derived recharge data from transmit drift compensation circuit 250 during the HOLD portion of the uplink telemetry transmission time period. The D/A converter responds by providing an analog control voltage to the FM INPUT of VCO 204 to make fine adjustments to the VCO carrier frequency output on line 206 in a manner described further below.

The RECEIVE control signal couples the antenna 28 to the input of the receiver 232 through switch 240, enables the receiver 232 to receive downlink transmitted, FSK modulated command data packets, and enables the operation of the AFC algorithm during the subsequent HOLD portion of the downlink telemetry transmission time period. The AFC algorithm can be embodied in digital logic, firmware or software, and for convenience of description is referred to herein as being carried out by an AFC algorithm circuit 236. The Rx AFC RECHARGE DATA developed by the AFC algorithm circuit 236 is directed to an Rx input of the D/A converter 238 during the HOLD portion of the downlink telemetry transmission time period. The RECEIVE control signal is also applied to the D/A converter to enable it to provide an analog control voltage to the FM INPUT of VCO 204 to make fine adjustments to the VCO carrier frequency output on line 206 in a manner described further below.

The LOCK/HOLD control signal is high (logic "1") during the LOCK portion and low (logic "0") during the HOLD portion of both the downlink and uplink telemetry transmission time periods, and is applied to either close or open switches 216 and 218 and to enable or disable the AFC algorithm circuit 232 and the D/A converter 238.

It is necessary to develop the carrier frequency and apply the carrier frequency to the transmitter 230 during the uplink telemetry transmission time period and to the receiver 232 during the downlink telemetry transmission time period. A frequency synthesizer 200 comprising a PLL circuit 202 and VCO 204 generates the carrier frequency on VCO line 206 during the initial LOCK portion of each uplink and downlink telemetry transmission time period. The PLL circuit 202 draws battery current at a high energy consuming rate as it stabilizes the carrier frequency output by VCO 204.

The VCO 204 has a voltage input VCOIN for controlling a nominal local carrier frequency at the VCO output line 206 dependent upon a control voltage stored in loop filter circuit 214 which is applied to VCOIN. The initial or LOCK portions of the uplink and downlink telemetry transmission time periods are commenced when the switches 216 and 218 are closed by the LOCK/HOLD control signal. The PLL circuit 202 is of the conventional type described in the above referenced '365 patent, for example, that comprises a 1/N frequency divider 208, a phase detector 210, and a charge pump 212 coupled between switch 218 and the capacitive loop filter 214. The PLL circuit 202 operates employing the VCO output carrier frequency on line 206, a programmed value "N" for the 1/N frequency divider 208, and a reference frequency. The reference frequency is preferably 50 kHz, and is derived by the frequency standard circuit 244 from the CLK signal of system clock 122 and divided by frequency divider 245.

The LOCK/HOLD command is supplied from the control and timing system 102 when telemetry is operational. The LOCK/HOLD signal closes switches 216 and 218 to apply the 50 kHz reference frequency and the carrier frequency generated by the VCO 204 to the PLL circuit 202 during the initial or LOCK portion of the uplink and downlink telemetry transmission time periods. Then, the LOCK/HOLD signal opens switches 216 and 218 to disconnect these signals from the PLL circuit 202 during the subsequent or HOLD portions of the uplink and downlink telemetry transmission time periods. Alternatively or additionally, one or more of the components of the PLL circuit 202 may be powered down during the HOLD portions of the uplink and downlink telemetry transmission time periods.

Thus, during each LOCK portion, phase detector 210 receives the 50 kHz reference frequency and the carrier frequency that is divided down by "N" in the 1/N circuit 208 and responds to the difference in phase between the two input signals to provide a charge pump control signal to the charge pump 212. The charge pump 212 responds to the magnitude of the charge pump control signal by charging or discharging a loop filter capacitor in loop filter circuit 214 to a VCOIN voltage. The charge pump control signal diminishes as the VCOIN voltage reaches a voltage sufficient to cause the VCO 204 to oscillate at the nominal local carrier frequency.

The LOCK/HOLD control signal changes state after the LOCK portion is either timed out by a timer or when the VCO generated carrier frequency stabilizes within an acceptable frequency tolerance from the nominal carrier frequency. The subsequent or HOLD portions of the uplink and downlink telemetry transmission time periods are commenced on the change in state of the LOCK/HOLD control signal. The switches 216 and 218 are opened by the change in state of the LOCK/HOLD control signal, and power may also be removed from certain of the PLL blocks.

PATIENT DATA uplink telemetry transmission commences following the change in state of the LOCK/HOLD control signal and is completed during the HOLD portion of the uplink telemetry transmission time period. During PATIENT DATA uplink telemetry transmission, the FSK modulator 220 develops an FSK input signal value corresponding to each "1" or "0" data bit, respectively, of the PATIENT DATA that is applied to the FM INPUT of VCO 204. The FSK input signal is a voltage that is effectively summed with the VCOIN voltage to increase or decrease the total voltage that the VCO responds to. The VCO 204 responds to the sum of the FSK input signal voltage at the FM INPUT and the VCOIN voltage by increasing or decreasing the carrier frequency with respect to the nominal carrier frequency otherwise effected solely by the control voltage at VCOIN. In this way, the VCO generated carrier frequency is frequency shifted to reflect each "1" or "0" binary data bit. The modulated carrier frequency is applied to transmitter 230 which transmits it through the T/R switch 240 and antenna 28.

A downlink telemetry transmission is received following the change in state of the LOCK/HOLD control signal and is completed during the HOLD portion of the downlink telemetry transmission time period. The receiver 232 is enabled by the RECEIVE control signal to receive the downlink transmitted, FSK modulated, carrier frequency through switch 240 and the VCO generated carrier frequency output on line 206. The instantaneous frequency difference between the downlink transmitted, FSK modulated, carrier frequency through switch 240 and the VCO generated carrier frequency output on line 206 is determined in receiver 232, and the difference is applied to the demodulator 234 and the AFC algorithm circuit 236. The instantaneous frequency difference changes at the data bit rate to reflect FSK modulation of the carrier frequency of the downlink transmitted, FSK modulated, carrier frequency, and the data bits are demodulated by demodulator 234. A data bit stream comprising the downlink telemetry data in each data packet is thereby output from the demodulator 234 and supplied to the control and timing system 102.

The control voltage stored on the capacitor of the loop filter circuit 214 is established in the LOCK portions of the uplink and downlink telemetry transmission time periods, but tends to dissipate as the capacitor discharges over time during the subsequent HOLD portions of the uplink and downlink telemetry transmission time periods and is not recharged by charge pump 212. Consequently, the carrier frequency generated by the VCO 204 on line 206 tends to drift away from the nominal carrier frequency established during the LOCK portions of the uplink and downlink telemetry transmission time periods, causing transmitting and receiving accuracy to suffer.

In addition, there may be a deviation that occurs at manufacture or develops over time from the nominal carrier frequency that the VCO is intended to oscillate at when a predetermined voltage is applied to VCOIN. It is desirable to maintain the VCO carrier frequency within a nominal tolerance of ±1,000 Hz, for example, of the transmitted carrier frequency, when the loop filter capacitor is charged during the LOCK portion. However, the actual frequency deviation between the VCO carrier frequency and the downlink transmitted carrier frequency may exceed the tolerance.

In accordance with one aspect of the present invention, the voltage stored by the loop filter capacitor of loop filter 204 is maintained by a recharge current provided by leakage compensation circuit 242. The leakage compensation circuit 242 is enabled at all times during both the LOCK and HOLD portions of each uplink and downlink telemetry transmission time period to provide a RECHARGE current that helps to maintain the carrier frequency generated by the VCO 204 within an acceptable frequency deviation tolerance during the HOLD portions to enable reliable uplink telemetry transmission. The RECHARGE current is derived by leakage compensation circuit 242 from RECHARGE DATA stored in memory in the control and timing system 102. The RECHARGE DATA is derived from a leakage rate observed during testing of the capacitive loop filter during fabrication of the IMD in IMD memory. The RECHARGE DATA is digitized and stored in a dedicated register in RAM in the control and timing system 102, and is retrieved and used by the leakage compensation circuit 242 to develop and apply the RECHARGE current to recharge said loop filter capacitor.

However, it is desirable to provide an even more accurate or finer control of the carrier frequency during the HOLD portions of the uplink and downlink telemetry transmission time periods. In accordance with a further aspect of the invention, the AFC algorithm circuit 236 is enabled by the state of the LOCK/HOLD and RECEIVE control signals during the HOLD portion of each downlink telemetry transmission time period. The AFC algorithm circuit 236 embodies an AFC algorithm in digital logic. The AFC algorithm circuit 236 samples the output of the receiver circuit 232 and determines a moving average frequency difference over two or more FSK modulation time periods to average out the FSK modulation of the downlink telemetered carrier frequency signal. The AFC algorithm then develops a digitized AFC correction value for the sample, and a stream of such digitized AFC correction values is developed over the HOLD portion of the downlink telemetry transmission time period. Each digitized AFC correction value is related to the sampled difference in frequency between each time sample of the received and VCO generated carrier frequencies averaged over a time period. Each AFC correction value represents a correction voltage, which when applied to the FM INPUT of VCO 204, causes the VCO 204 to change frequency and reduce the frequency difference.

During the HOLD portions of the downlink telemetry transmission time period, each digitized AFC correction value that is generated by the AFC algorithm circuit 236 is applied in real time to an input of the DIA converter 238. DIA converter 238 is enabled by the RECEIVE and LOCK/HOLD control signals to convert each real time generated, digitized, AFC correction value into a correction voltage that is applied to the FM INPUT of VCO 204 until the next in time digitized AFC correction value is received from the AFC algorithm circuit 236. In this case, the correction voltage from D/A converter 238 is effectively summed with the VCOIN voltage to increase or decrease the total voltage that the VCO 204 responds to.

Figure 6:
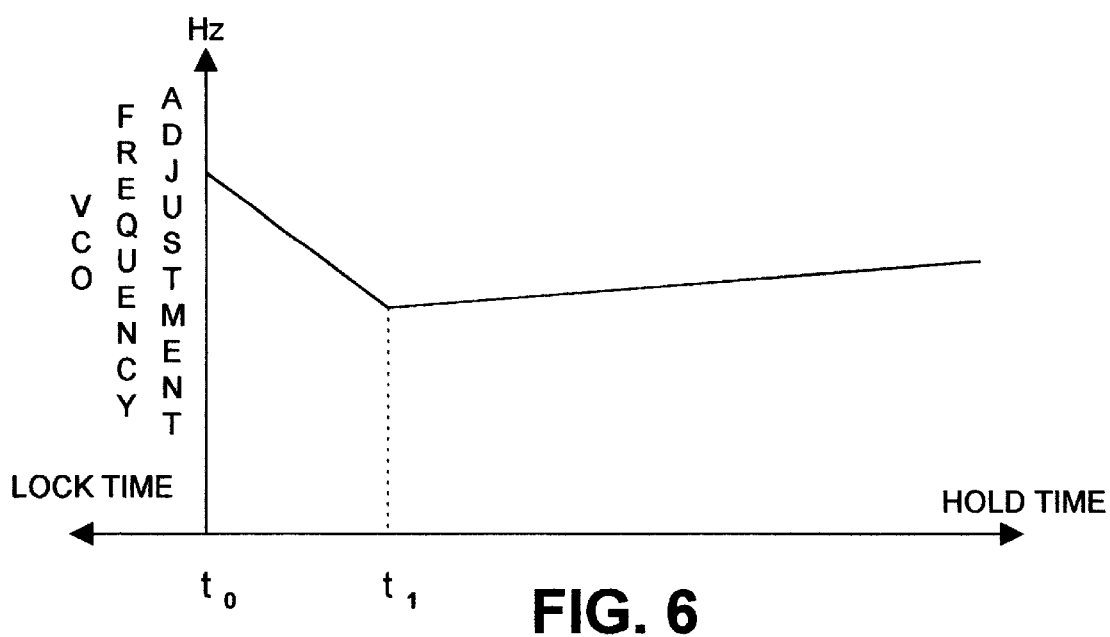
FIG. 6 is a timing diagram illustrating the operation of the AFC algorithm.

FIG. 6 illustrates how the frequency adjustment of the VCO 204 occurs during the HOLD portion of the downlink telemetry transmission time period starting at time $t_0$ At time $t_0$ the deviation between the VCO generated carrier frequency and the downlink telemetry transmitted carrier frequency may be relatively great, due to the above-mentioned deviation by the VCO from the nominal carrier frequency that can occur. Consequently, the AFC correction value developed by the AFC algorithm may initially be fairly large and the change in frequency over the time period $t_0$ to $t_1$ reflects the adjustment that occurs to decrease the frequency difference toward zero. Then, the slow discharge of the loop filter capacitor starts to influence the VCO generated carrier frequency. Therefore, the frequency adjustments that are necessary to drive the VCO generated carrier frequency into alignment with the average value of the downlink telemetry transmitted carrier frequency tend to increase in magnitude, as shown in FIG. 6 after $t_1$.

During the HOLD portion of the downlink telemetry transmission time period, each AFC correction value of the data set of digitized AFC correction values that is developed by the AFC algorithm following time ti is processed in the transmit drift compensation circuit 250. During the uplink telemetry transmission, the slope of the frequency adjustments that are necessary to drive the VCO generated carrier frequency into alignment with the average value of the downlink telemetry transmitted carrier frequency is determined, and a further digitized correction value is determined and applied to an input of the D/A converter 238. D/A converter 238 is enabled by the TRANSMIT and LOCK/HOLD control signals to convert each correction value into a correction voltage that is applied to the FM INPUT of VCO 204 until the next in time digitized correction value is applied. In this case, the correction voltage from D/A converter 238 and the FSK input signal from FM modulator 220 are summed together within the FM INPUT, and the summed voltages are then effectively summed with the VCOIN voltage to increase or decrease the total voltage that the VCO 204 responds to. The VCO 204 responds to the sum of the FSK input signal voltage, the correction voltage and the VCOIN voltage to accurately maintain the VCO output carrier frequency within acceptable tolerances while maintaining accurate FSK modulation of the VCO output carrier frequency to reflect each "1" or "0" binary data bit. This enables maintenance of the carrier frequency generated by the VCO 204 within an acceptable frequency deviation tolerance enabling reliable uplink telemetry transmission of the PATIENT DATA applied to the FM input of the VCO 204.

Turning to FIG. 5, it depicts the above-described states of operation and the transitions between the states wherein typically a telemetry session comprises one or more sequence of a downlink telemetry transmission followed by an uplink telemetry transmission. In the IDLE state prior to or following completion of a telemetry session, the RECEIVE, TRANSMIT, and LOCK/HOLD control signals are logic low, the frequency synthesizer 200 does not develop any carrier frequency on line 206, and the leakage compensation circuit 242 is powered down. When the LOCK/HOLD and RECEIVE control signals go high, the state transition "A" takes place from the IDLE state to the Rx PLL LOCK state, wherein the leakage compensation circuit 242 is operational, the VCO 204 and PLL circuit 202 are connected together, and the frequency synthesizer 200 begins to operate as described above. The Rx PLL LOCK state is maintained in loop "B" until the VCO output carrier frequency is stabilized as described above. Then, when the LOCK/HOLD control signal goes low, the Rx HOLD state is entered through state transition "C", and the AFC algorithm is commenced to provide the real-time AFC correction values to the D/A converter 238. The Rx HOLD state continues through the duration of the HOLD portion via loop "D" until the RECEIVE control signal goes low.

Then, the TRANSMIT control signal goes high and the LOCK/HOLD control signal goes high again, causing the state transition "E" to the Tx PLL LOCK state. Again, the leakage compensation circuit 242 is operational, the VCO 204 and PLL circuit 202 are connected together, and the frequency synthesizer 200. begins to operate as described above. The Tx PLL LOCK state is maintained in loop "F" until the VCO output carrier frequency is stabilized as described above. Then, when the LOCK/HOLD control signal goes low, the Tx HOLD state is entered through state transition "G", and the D/A converter 238 receives the stored AFC correction values to provide the drift compensation to the FM INPUT of VCO 204 as described above. The Tx HOLD state with the drift compensation continues through the duration of the HOLD portion via loop "H" until the TRANSMIT control signal goes low.

Then, the transition "I" is made back to the Rx PLL LOCK state to repeat the state changes of each uplink and downlink telemetry transmission of the telemetry session until all are completed, and the final transition "J" to the IDLE state is made. The IDLE state loop J continues until the next downlink telemetry transmission.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. In a battery powered, implantable medical device (IMD) adapted to be implanted in a patient's body to provide a therapy delivery and/or monitoring function, telemetry transceiver circuitry for uplink telemetry transmission of IMD developed patient data from the IMD during a predetermined uplink telemetry transmission time period and downlink telemetry reception of downlink telemetry data during a predetermined downlink telemetry transmission time period, said IMD further comprising:

a voltage-controlled oscillator (VCO) having a VCO voltage input for developing an FM telemetry carrier frequency at a VCO output dependent upon a control voltage applied to the VCO voltage input and a VCO frequency modulation (FM) input that receives a data bit modulation voltage that modulates the VCO generated carrier frequency during uplink transmission of patient data;

a phase-lock loop (PLL) circuit having a PLL input adapted to selectively receive the carrier frequency at the VCO output and to supply a control voltage to said capacitive loop filter a loop filter circuit that is coupled to the VCO voltage control input;

telemetry control means operable upon initiation of an uplink or downlink telemetry transmission for operating said VCO with said PLL circuit and said loop filter as a frequency synthesizer in a high battery energy consumption state for an initial LOCK portion of the uplink telemetry transmission time period to establish a frequency lock control voltage stored by said loop filter circuit and applied to said VCO voltage input to cause said VCO to generate a frequency locked carrier signal at said VCO output;

means for selectively de-coupling said PLL circuit from said VCO and applying patient data to said FM input during a subsequent HOLD portion of an uplink telemetry transmission time period; and voltage hold means operable during the HOLD portion of the uplink telemetry transmission time period for establishing a frequency correction voltage at the VCO FM input which modulates the VCO generated carrier frequency in a manner that compensates for drift in the VCO generated carrier frequency to maintain the VCO generated carrier frequency within an acceptable frequency deviation tolerance enabling reliable uplink telemetry transmission of patient data.

2. The IMD of claim 1, wherein said capacitive loop filter circuit voltage tends to dissipate over time at a predetermined rate as said loop filter capacitor discharges during said HOLD portion of said uplink telemetry transmission time period, and further comprising recharging means for recharging said loop filter capacitor to offset the discharge thereof.

3. The IMD of claim 2, further comprising:

means for storing a recharge current value derived from a leakage rate observed during testing of the capacitive loop filter during fabrication of the IMD in IMD memory; and wherein:

said recharging means retrieves from IMD memory and uses said recharge current value it to develop and apply a recharge current value to said loop filter capacitor to recharge said loop filter capacitor.

4. The IMD of claim 1, further comprising:

automatic frequency control (AFC) means responsive to the difference between a received carrier frequency signal received from the remote medical device and the carrier frequency generated by the VCO during the HOLD portion of the downlink telemetry transmission time period for establishing an AFC correction value varying as a function of the difference between the received carrier frequency signal received from the remote medical device and the carrier frequency generated by the VCO; and converting means for converting the AFC correction value to a frequency correction voltage and applying the frequency correction voltage to the FM input of said VCO during the HOLD portion of the downlink telemetry transmission time period to maintain the VCO generated carrier frequency within an acceptable frequency deviation tolerance enabling reliable downlink telemetry reception of downlink telemetry data.

5. The IMD of claim 4, wherein said capacitive loop filter circuit voltage tends to dissipate over time at a predetermined rate as said loop filter capacitor discharges during said HOLD portion of said downlink telemetry transmission time period, and further comprising recharging means for recharging said loop filter capacitor to offset the discharge thereof.

6. The IMD of claim 5, further comprising:

means for storing a recharge current value derived from a leakage rate observed during testing of the capacitive loop filter during fabrication of the IMD in IMD memory; and wherein:

said recharging means retrieves from IMD memory and uses said recharge current value to develop and apply a recharge current value to said loop filter capacitor to recharge said loop filter capacitor.

7. The IMD of claim 6, wherein said voltage hold means further comprises means responsive to the AFC correction value established by the AFC means during the HOLD portion of the downlink telemetry transmission time period and operable during the HOLD portion of the uplink telemetry transmission time period for establishing a frequency correction voltage at the VCO FM input which modulates the VCO generated carrier frequency in a manner that compensates for drift in the VCO generated carrier frequency to maintain the VCO generated carrier frequency within an acceptable frequency deviation tolerance enabling reliable uplink telemetry transmission of patient data.

8. The IMD of claim 4, wherein said voltage hold means further comprises means responsive to the AFC correction value established by the AFC means during the HOLD portion of the downlink telemetry transmission time period and operable during the HOLD portion of the uplink telemetry transmission time period for establishing a frequency correction voltage at the VCO FM input which modulates the VCO generated carrier frequency in a manner that compensates for drift in the VCO generated carrier frequency to maintain the VCO generated carrier frequency within an acceptable frequency deviation tolerance enabling reliable uplink telemetry transmission of patient data.

9. In a battery powered, implantable medical device (IMD) adapted to be implanted in a patient's body to provide a therapy delivery and/or monitoring function, a method of providing uplink telemetry transmission of IMD developed patient data from the IMD during a predetermined uplink telemetry transmission time period and downlink telemetry reception of downlink telemetry data during a predetermined downlink telemetry transmission time period, said method further comprising the steps of:

within the IMD, providing a transceiver comprising a transmitter, a receiver, a voltage-controlled oscillator (VCO) having a voltage input and a frequency modulation (FM) input for developing an FM telemetry carrier frequency at a VCO output dependent upon a control voltage applied to the voltage input and an FM input signal applied to the FM input, and a phase-lock loop (PLL) circuit having a PLL input adapted to selectively receive the carrier frequency at the VCO output and to supply a control voltage to a capacitive loop filter circuit that is coupled to the VCO voltage input;

upon initiation of an uplink telemetry transmission, operating said VCO with said PLL circuit and said loop filter as a frequency synthesizer in a high battery energy consumption state for an initial LOCK portion of the uplink telemetry transmission time period to establish a frequency lock control voltage stored by said loop filter circuit and applied to said VCO voltage input to cause said VCO to generate a frequency locked carrier signal at said VCO output applied to said transmitter;

de-coupling said PLL circuit from said VCO and applying patient data to said FM input during a HOLD portion of the uplink telemetry transmission time period;and providing a frequency correction voltage to said FM input during the HOLD portion of the uplink telemetry transmission time that is sufficient to maintain a carrier frequency generated by said VCO at said VCO output within an acceptable frequency deviation tolerance enabling reliable uplink telemetry transmission of patient data.

10. The method of claim 9, wherein said capacitive loop filter circuit voltage tends to dissipate over time at a predetermined rate as a loop filter capacitor discharges during said uplink telemetry transmission time period, and the providing step further comprises recharging said capacitor to offset the discharge thereof.

11. The method of claim 10, wherein the providing step further comprises the steps of:

storing a recharge current value derived from a leakage rate observed during testing of the capacitive loop filter during fabrication of the IMD in IMD memory; and retrieving said recharge current value from IMD memory and applying a recharge current to said loop filter capacitor.

12. The method of claim 11, further comprising the steps operable upon reception of a downlink telemetry transmission of a downlink telemetry data modulated carrier frequency signal by said receiver of:

operating said VCO coupled with said PLL circuit and said loop filter as a frequency synthesizer in a high battery energy consumption state for an initial LOCK portion of the downlink telemetry transmission time period to establish a frequency lock control voltage stored by said loop filter circuit and applied to said VCO voltage input to cause said VCO to generate a frequency locked carrier signal at said VCO output;

de-coupling said PLL circuit from said VCO during a subsequent HOLD portion of the downlink telemetry transmission time period;

providing a received carrier signal upon receipt of the downlink telemetry data modulated carrier frequency signal;

generating a frequency correction voltage from the difference in frequency between the received carrier frequency signal and the carrier frequency generated by the VCO during the HOLD portion of the downlink telemetry transmission time period; and applying the frequency correction voltage to the FM input of said VCO during the HOLD portion of the downlink telemetry transmission to provide automatic frequency control of the carrier frequency generated by the VCO.

13. The method of claim 12, wherein the generating step further comprises the steps of:

applying an automatic frequency control (AFC) algorithm to the frequency difference between the received carrier frequency signal received from the remote medical device and the carrier frequency generated by the VCO during the HOLD portion of the downlink telemetry transmission time period to establish an AFC correction value varying as a function of the difference between the received carrier frequency signal received from the remote medical device and the carrier frequency generated by the VCO; and converting the AFC correction value to a frequency correction voltage value.

14. The method of claim 13, further comprising the steps of:

establishing a frequency correction voltage from the AFC correction value derived during the HOLD portion of the downlink telemetry transmission time period; and applying the frequency correction voltage to the FM input of said VCO during the HOLD portion of an uplink telemetry transmission time period to modulate the VCO generated carrier frequency in a manner that compensates for drift in the VCO generated carrier frequency to maintain the VCO generated carrier frequency within an acceptable frequency deviation tolerance enabling reliable uplink telemetry transmission of patient data.

15. The method of claim 9, further comprising the steps operable upon reception of a downlink telemetry transmission of a downlink telemetry data modulated carrier frequency signal by said receiver of:

operating said VCO coupled with said PLL circuit and said loop filter as a frequency synthesizer in a high battery energy consumption state for an initial LOCK portion of the downlink telemetry transmission time period to establish a frequency lock control voltage stored by said loop filter circuit and applied to said VCO voltage input to cause said VCO to generate a frequency locked carrier signal at said VCO output;

de-coupling said PLL circuit from said VCO during a subsequent HOLD portion of the downlink telemetry transmission time period;

providing a received carrier signal upon receipt of the downlink telemetry data modulated carrier frequency signal;

generating a frequency correction voltage from the difference in frequency between the received carrier frequency signal and the carrier frequency generated by the VCO during the HOLD portion of the downlink telemetry transmission time period; and applying the frequency correction voltage to the FM input of said VCO during the HOLD portion of the downlink telemetry transmission to provide automatic frequency control of the carrier frequency generated by the VCO.

16. The method of claim 15, wherein the generating step further comprises the steps of:

applying an automatic frequency control (AFC) algorithm to the frequency difference between the received carrier frequency signal received from the remote medical device and the carrier frequency generated by the VCO during the HOLD portion of the downlink telemetry transmission time period to establish an AFC correction value varying as a function of the difference between the received carrier frequency signal received from the remote medical device and the carrier frequency generated by the VCO; and converting the AFC correction value to a frequency correction voltage value.

17. The method of claim 16, further comprising the steps of:

establishing a frequency correction voltage from the AFC correction value derived during the HOLD portion of the downlink telemetry transmission time period; and applying the frequency correction voltage to the FM input of said VCO during the HOLD portion of an uplink telemetry transmission time period to modulate the VCO generated carrier frequency in a manner that compensates for drift in the VCO generated carrier frequency to maintain the VCO generated carrier frequency within an acceptable frequency deviation tolerance enabling reliable uplink telemetry transmission of patient data.

18. A method of conserving energy during uplink and downlink telemetry transmissions of data between a remote device and an implantable medical device (IMD) employing frequency modulation of a predetermined carrier frequency, comprising the steps of:

providing, in the IMD, a phase-lock loop (PLL) circuit having a capacitive loop filter connected to a control voltage input of a voltage-controlled oscillator (VCO), an output of said VCO providing a carrier signal as a function of a control voltage of the capacitive loop filter during uplink and downlink telemetry transmissions;

during an initial LOCK portion of an uplink or downlink telemetry transmission, operating said PLL circuit, said VCO, and said loop filter as a voltage synthesizer in a phase-lock process long enough to charge a capacitor of the capacitive loop filter to a control voltage sufficient to cause said VCO to generate a carrier frequency within a selected acceptable frequency deviation tolerance from the predetermined carrier frequency;

during a subsequent HOLD portion of an uplink or downlink telemetry transmission applying the control voltage to the VCO; and during the HOLD portion of a downlink telemetry transmission:

generating a frequency correction voltage from the difference in frequency between the received carrier frequency signal and the carrier frequency generated by the VCO; and applying the frequency correction voltage to the FM input of said VCO to provide automatic frequency control of the carrier frequency generated by the VCO.

19. The method of claim 18, further comprising the step of providing a frequency correction voltage to said FM input during the HOLD portion of the uplink telemetry transmission time that is sufficient to maintain a carrier frequency generated by said VCO at said VCO output within an acceptable frequency deviation tolerance enabling reliable uplink telemetry transmission of patient data.

20. The method of claim 19, wherein said capacitive loop filter circuit voltage tends to dissipate over time at a predetermined rate as a loop filter capacitor discharges during uplink and downlink telemetry transmission time periods, and the providing step further comprises recharging said capacitor to offset the discharge thereof during the uplink and downlink telemetry transmission time periods.

21. The method of claim 20, wherein the providing step further comprises the steps of:

storing a recharge current value derived from a leakage rate observed during testing of the capacitive loop filter during fabrication of the IMD in IMD memory; and retrieving said recharge current value from IMD memory and applying a recharge current to said loop filter capacitor.

22. In a battery powered, implantable medical device (IMD) adapted to be implanted in a patient's body to provide a therapy delivery and/or monitoring function, telemetry transceiver circuitry for uplink telemetry transmission of IMD developed patient data from the IMD during a predetermined uplink telemetry transmission time period and downlink telemetry reception of programming and interrogation commands during a predetermined downlink telemetry transmission time period, said IMD further comprising:

a voltage-controlled oscillator (VCO) having a voltage input and a frequency modulation (FM) input for developing an FM telemetry carrier frequency at a VCO output dependent upon a control voltage applied to the voltage input and an FM input signal applied to the FM input;

a capacitive loop filter circuit coupled to the VCO voltage control input for providing a control voltage, said capacitive loop filter circuit comprising a capacitor;

a phase-lock loop (PLL) circuit having a PLL input adapted to selectively receive the carrier frequency at the VCO output and to supply a control voltage to a capacitive loop filter circuit that is coupled to the VCO voltage input;

uplink telemetry control means operable upon initiation of an uplink telemetry transmission or reception of a downlink telemetry transmission for operating said VCO with said PLL circuit and said loop filter as a frequency synthesizer in a high battery energy consumption state for a LOCK portion of the uplink telemetry transmission time period to establish a frequency lock control voltage stored by said loop filter circuit and applied to said VCO voltage input to cause said VCO to generate a frequency locked carrier signal at said VCO output;

means operable during a HOLD portion of an uplink or downlink telemetry transmission for applying the control voltage to the VCO;

means operable during the HOLD portion of an uplink telemetry transmission for providing a frequency hold control voltage to the loop filter circuit that is sufficient to maintain a frequency hold carrier frequency generated by said VCO at said VCO output within an acceptable frequency deviation tolerance enabling reliable uplink telemetry transmission of patient data; and means operable during the HOLD portion of a downlink telemetry transmission for:
  generating a frequency correction voltage from the difference in frequency between the received carrier frequency signal and the carrier frequency generated by the VCO; and
  applying the frequency correction voltage to the FM input of said VCO to provide automatic frequency control of the carrier frequency generated by the VCO.

23. The IMD of claim 22 further comprising:

voltage hold means coupled with said loop filter circuit and operable during the HOLD portion of the uplink telemetry transmission time period for establishing a frequency correction voltage at the VCO FM input which modulates the VCO generated carrier frequency in a manner that compensates for drift in the VCO generated carrier frequency to maintain the VCO generated carrier frequency within an acceptable frequency deviation tolerance enabling reliable uplink telemetry transmission of patient data.

24. The IMD of claim 22, wherein said capacitive loop filter circuit voltage tends to dissipate over time at a predetermined rate as said loop filter capacitor discharges during said HOLD portion of said uplink telemetry transmission time period, and further comprising recharging means for recharging said loop filter capacitor to offset the discharge thereof.

25. The IMD of claim 24, further comprising:

means for storing a recharge current value derived from a leakage rate observed during testing of the capacitive loop filter during fabrication of the IMD in IMD memory; and wherein:

said recharging means retrieves from IMD memory and uses said recharge current value to develop and apply a recharge current value to said loop filter capacitor to recharge said loop filter capacitor.

* * * * *